(12) United States Patent
Yagi et al.

(10) Patent No.: US 10,786,165 B2
(45) Date of Patent: Sep. 29, 2020

(54) BLOOD-FLOW ANALYSIS DEVICE FOR BLOOD-FLOW SIMULATION AND METHOD THEREFOR

(71) Applicant: EBM CORPORATION, Tokyo (JP)

(72) Inventors: Takanobu Yagi, Tokyo (JP); Young-Kwang Park, Tokyo (JP)

(73) Assignee: EBM CORPORATION, Tokyo (JP)

( * ) Notice: Subject to any disclaimer, the term of this patent is extended or adjusted under 35 U.S.C. 154(b) by 843 days.

(21) Appl. No.: 15/503,618

(22) PCT Filed: Oct. 8, 2015

(86) PCT No.: PCT/JP2015/078693
§ 371 (c)(1),
(2) Date: Jul. 28, 2017

(87) PCT Pub. No.: WO2016/056641
PCT Pub. Date: Apr. 14, 2016

(65) Prior Publication Data
US 2017/0360311 A1    Dec. 21, 2017

Related U.S. Application Data

(60) Provisional application No. 62/061,418, filed on Oct. 8, 2014.

(51) Int. Cl.
*A61B 5/00* (2006.01)
*A61B 5/026* (2006.01)
*A61B 5/021* (2006.01)
*A61B 5/0285* (2006.01)

(52) U.S. Cl.
CPC .............. *A61B 5/026* (2013.01); *A61B 5/004* (2013.01); *A61B 5/0073* (2013.01); *A61B 5/0261* (2013.01); *A61B 5/0263* (2013.01); *A61B 5/0285* (2013.01); *A61B 5/02108* (2013.01); *A61B 5/0066* (2013.01); *A61B 5/7282* (2013.01); *A61B 2576/02* (2013.01)

(58) Field of Classification Search
CPC ............................... A61B 5/026; A61B 5/004
See application file for complete search history.

(56) References Cited

FOREIGN PATENT DOCUMENTS

| JP | 2003-144395 A | 5/2003 |
|---|---|---|
| JP | 2004-321390 A | 11/2004 |
| JP | 2013-208158 A | 10/2013 |

OTHER PUBLICATIONS

International Search Report issued to PCT/JP2015/078693.
(Continued)

*Primary Examiner* — Joseph M Santos Rodriguez
(74) *Attorney, Agent, or Firm* — Taro Yaguchi

(57) ABSTRACT

The present method is a method for executing a computational fluid analysis on a blood flow at a blood vessel region to be analyzed, and displaying the analysis results, comprising the steps of: obtaining, by a computer, a vascular diameter (d) of an inlet and/or outlet of a blood vessel region to be analyzed from medical images which include said blood vessel region; obtaining, by the computer, an estimated flow rate (Q) at the inlet and/or outlet based on the vascular diameter (d); and applying, by the computer, the estimated flow rate (Q) to a blood flow characteristics pattern of said blood vessel region and outputting blood flow characteristics at the inlet and/or outlet of the analysis object site.

18 Claims, 10 Drawing Sheets

(56) References Cited

OTHER PUBLICATIONS

K. Zarins et al, Shear stress regulation of artery lumen diameter in experimental atherogenesis, J of Vascular Surgery, 1985.
Translation of Written Opinion of the International Searching Authority issued to PCT/JP2015/078693.

(a)

| Name | Appropriate wall surface shear stress (Pa) |
|---|---|
| Standard value A | 1.5 |
| Standard value B | 3.0 |
| Standard value C | 5.0 |
| Arteriosclerosis (+) | ×1.2 |
| Arteriosclerosis (++) | ×1.5 |
| High blood pressure (+) | ×1.3 |
| High blood pressure (++) | ×1.6 |

(b)

(a)

| | Name | Blood viscosity μ (cP) |
|---|---|---|
| Baselines | Standard value A | 4.0 |
| | Standard value B | 5.5 |
| | Standard value C | 6.0 |
| Hematologic diseases | Hyperlipemia (+) | ×1.2 |
| | Hyperlipemia (++) | ×1.4 |
| | Diabetes (+) | ×1.3 |
| | Diabetes (++) | ×1.8 |
| Drug administration | Antiplatelet agent | ×0.8 |
| | Anticoagulant | ×0.7 |
| Object blood vessels | Large and medium arteries | ×1 |
| | Small arteries | ×2.3 |
| | Arterioles | ×4.7 |

(a)

(b)

| | | ICA | MCA | ACA |
|---|---|---|---|---|
| Average flow rate (ml/min) | Reference values* | 252±52 | 145±27 | 80±28 |
| | Calculated values | 225 | 126 | 80.4 |
| Flow rate distribution ratio | Reference values* | 3.15 | 1.81 | 1 |
| | Calculated values | 2.79 | 1.56 | 1 |

* Regional cerebral blood flow using quantitative MR angiography,
M. Zhao et al., AJNR, 2007

BLOOD-FLOW ANALYSIS DEVICE FOR BLOOD-FLOW SIMULATION AND METHOD THEREFOR

CROSS REFERENCE TO RELATED APPLICATIONS

This application claims the benefit of U.S. Provisional Application No. 62/061,418, filed on Oct. 8, 2014. The entire disclosure of the aforesaid application is incorporated herein by reference.

FIELD OF THE INVENTION

The present invention relates to a method for estimating a boundary condition, one of inputs for a blood flow analysis with Computational Fluid Dynamics (CFD), and a blood flow analysis apparatus comprising a function to automatically set a boundary condition based on the estimated boundary condition.

BACKGROUND OF THE INVENTION

Blood flow analysis is one of the techniques conventionally conducted. One of the techniques to conduct the blood flow analyses is to use Computational Fluid Dynamics (CFD) to perform computer processing. When the CFD is calculated with computer processing, there is no program or the like having a function to automatically set a boundary condition as an input to a blood flow analysis, and it has been required to manually enter and set actual measurement values for each blood vessel of each patient.

In general, boundary conditions in blood flow analyses are given based on (1) actual measurement values obtained with the phase-contrast MRI method and/or the ultrasonic Doppler method and (2) statistical average values based on the measurements.

However, (1) is time-consuming and costly, and (2) has no proven effectiveness regarding application to patients since only known standard values are ones provided by volunteers. Therefore, even the manual setting has a limitation.

Thus, there is a need for a technology for automatically setting the CFD boundary conditions and various developments have been conducted to that end.

However, intravascular blood flow is a pulsatile flow fluctuating over time. Blood vessels are flexible conduit lines and temporal fluctuation characteristics vary depending on individual vessels. For example, in aortas, blood is transported only during cardiac systole and there is no blood flow during cardiac diastole. Whereas, in brain arteries, vessel contractions and dilations serve to pump the blood and therefore, the blood flow never decreases to zero even during systole. It has been difficult to automatically configure a blood flow analysis apparatus with boundary condition setting taking into account such pulsatile blood flows, temporal fluctuations and differences among individual vessels.

For example, the following need to be considered when setting the boundary condition.

In general, vascular luminal surfaces have vascular endothelial cells. Vascular endothelial cells have a function to sense mechanical stimulation by the blood flow and a function to change the cells' biochemical reaction according to the mechanical stimulation value. More specifically, there is considered to be an appropriate wall surface shear stress for the endothelial cells, and if the wall surface shear stress deviates from its normal value, the endothelial cells contract or expand the vascular diameter and adjust the blood vessel shape.

In order to set the boundary condition, the above vascular physiological functions need to be considered, and the method to do so is limited to ones validated for boundary condition universality using animal studies (Reference 1: K. Zarins et al, Shear stress regulation of artery lumen diameter in experimental atherogenesis, J of VASCULAR SURGERY, 1985). According to Reference 1, the appropriate value of wall surface shear stress is known to be about 1.5 Pa. However, the range in which this appropriate value may be applied has not been clarified. For example, Reference 1 reports 1.5 Pa as the appropriate value, but this value was derived from an implicit premise of a blood viscosity $\mu=3.5$ cP. Also, this result was obtained only based on an animal study with primates as subjects. Hemodynamics of actual patients are influenced by aging advancement and medical conditions, and functions of vascular endothelial cells and blood viscosity themselves are known to degenerate due to those factors, limiting the applicability of the above appropriate value of wall surface shear stress.

The present inventors developed appropriate settings of the wall surface shear stress based on human clinical research studies, and as a result, completed a system and a method for allowing automatic setting of the boundary condition for blood flow analyses.

SUMMARY OF THE INVENTION

In order to overcome the above challenges, according to a first principal aspect of the present invention, there is provided a method for executing a computational fluid analysis on a blood flow in a blood vessel region to be analyzed, and displaying the analysis results, comprising the steps of: obtaining, by a computer, a vascular diameter (d) of an inlet and/or outlet of a blood vessel region to be analyzed from medical images which include said blood vessel region; obtaining, by the computer, an estimated flow rate (Q) at the inlet and/or outlet based on the vascular diameter (d); and applying, by the computer, the estimated flow rate (Q) to a blood flow characteristics pattern of said blood vessel region and outputting blood flow characteristics at the inlet and/or outlet of said blood vessel region.

According to one embodiment of the present invention, this method further comprises the step of: causing a user, by the computer, to selectively enter an aging advancement, a medical condition, a heart rate and/or an object blood vessel type of a patient as a subject of the blood flow analysis, wherein the blood flow characteristics pattern is an individualized pattern prepared according to the user-entered aging advancement, medical condition, heart rate and/or object blood vessel type of the patient, and wherein the outputting the blood flow characteristics step is performed by outputting the blood flow characteristics using the blood flow characteristics pattern according to the user-entered aging advancement, medical condition, heart rate and/or object blood vessel type of the patient.

According to another embodiment, the blood flow characteristics pattern is provided to define a relationship between a non-dimensional flow rate on one axis and a non-dimensional time on the other axis.

According to yet another embodiment of the present invention, the obtaining the estimated flow rate (Q) step comprises obtaining the estimated flow rate (Q) based on a cube of the vascular diameter ($d^3$).

In this case, the obtaining the estimated flow rate (Q) step preferably obtains the estimated flow rate (Q) based on the following formula:

$$Q=(\tau\times\pi/32\mu)d^3$$

(Here, $\tau$ is an appropriate wall surface shear stress and $\mu$ is a blood viscosity.)

Also, it is preferable that the present system further comprises: causing a user, by the computer, to enter an aging advancement, a medical condition, a heart rate and/or an object blood vessel type of a patient as a subject of the blood flow analysis; and determining, by the computer, the appropriate wall surface shear stress ($\tau$) and/or the blood viscosity ($\mu$) based on the user-entered aging advancement, medical condition, heart rate and/or object blood vessel type of the patient.

Moreover, the determining the appropriate wall surface shear stress ($\tau$) and/or the blood viscosity ($\mu$) step preferably uses an appropriate shear stress template and/or a blood characteristics template, which is normalized for each of the aging advancement, medical condition, heart rate and/or object blood vessel type of the patient.

According to still another embodiment of the present invention, the vascular diameter (d) is calculated by the computer as an equivalent diameter of an assumed circle having an identical area with a measured area of a plane orthogonal to a blood vessel centerline, wherein an average value or a median is used for the equivalent diameter.

According to another embodiment, the blood flow characteristics pattern is a temporal flow rate fluctuation pattern, and the blood flow characteristics is a temporal flow rate fluctuation.

According to a second principal aspect of the present invention, there is provided a blood flow analysis apparatus for executing a computational fluid analysis on a blood flow in a blood vessel region to be analyzed, and displaying the analysis results, comprising: a vascular diameter calculation section for obtaining, by a computer, a vascular diameter (d) of an inlet and/or outlet of a blood vessel region to be analyzed from medical images which include said blood vessel region; a blood vessel characteristics calculation section for obtaining, by the computer, an estimated flow rate (Q) at the inlet and/or outlet based on the vascular diameter (d); and a blood flow characteristics calculation section for applying, by the computer, the estimated flow rate (Q) to a blood flow characteristics pattern of said blood vessel region and outputting blood flow characteristics at the inlet and/or outlet of said blood vessel region.

According to a third principal aspect of the present invention, there is provided a computer software program for executing a computational fluid analysis on a blood flow at a blood vessel region to be analyzed, and displaying the analysis results, said computer software program comprising instructions for executing the steps of: obtaining, by a computer, a vascular diameter (d) of an inlet and/or outlet of a blood vessel region to be analyzed from medical images which include said blood vessel region; obtaining, by the computer, an estimated flow rate (Q) at the inlet and/or outlet based on the vascular diameter (d); and applying, by the computer, the estimated flow rate (Q) to a blood flow characteristics pattern of said blood vessel region and outputting blood flow characteristics at the inlet and/or outlet of said blood vessel region.

Note that characteristics of the present invention which were not listed above will be provided in the following description of embodiments and drawings of the present invention so that the characteristics are readily implementable by those skilled in the art.

DETAILED DESCRIPTION OF THE INVENTION

One preferred embodiment of the present invention will be described in detail below.

Figure 1:
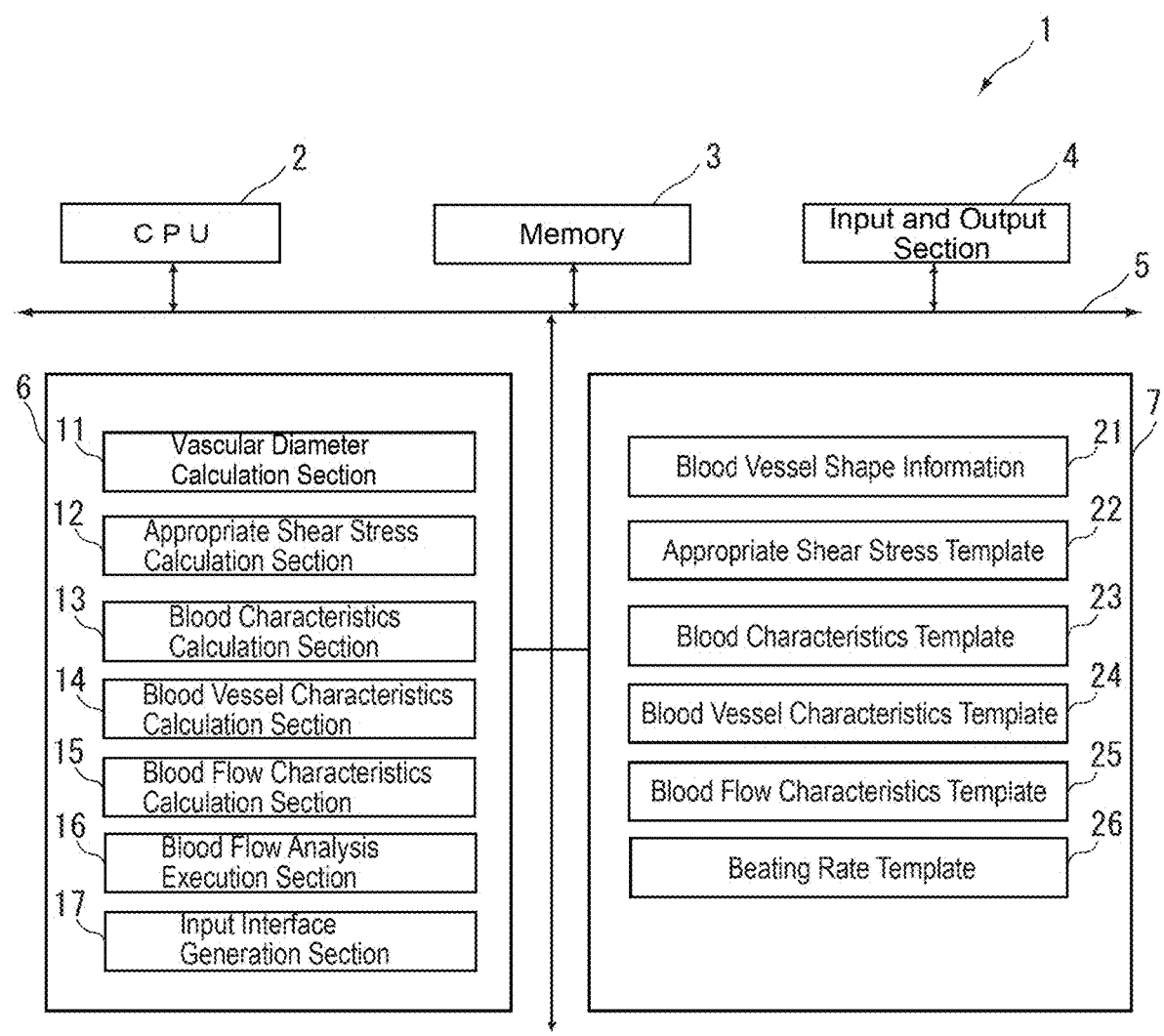
FIG. 1 is a schematic structural view showing one embodiment of the present invention.
Figure 2:
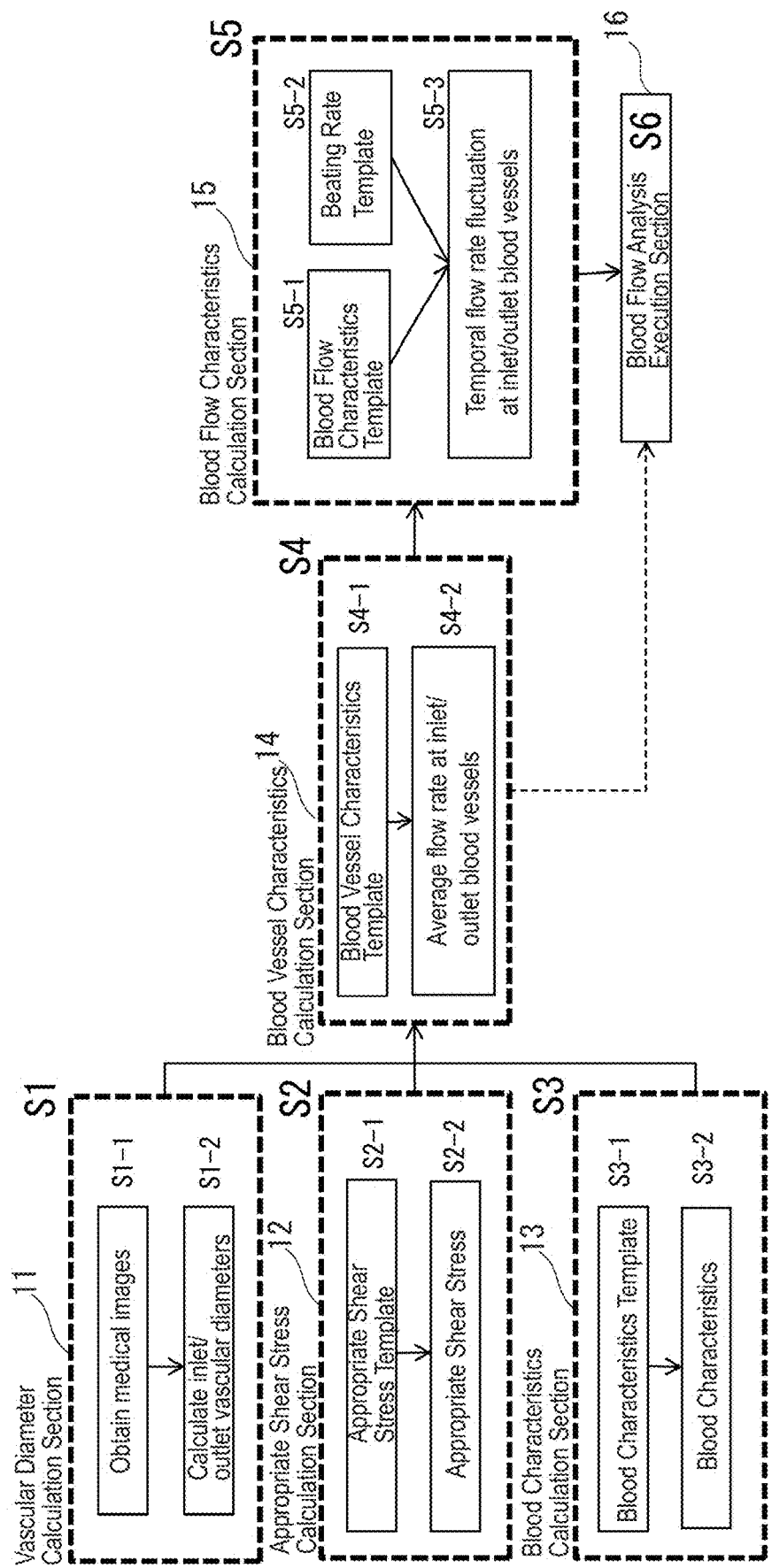
FIG. 2 is a flowchart showing processing steps in the present embodiment.

FIG. 1 is a schematic structural view showing a blood flow analysis device according to this embodiment.

The blood flow analysis device 1 is defined by a CPU 2, a memory 3 and an input and output section 4, which are connected with a bus 5, which in turn is connected with a program storage section 6 and a data storage section 7 for storing data such as various templates and the like. The program storage section 6 is provided with a vascular diameter calculation section 11 for calculating a vascular diameter of an object blood vessel from blood vessel shape information 21, an appropriate shear stress calculation section 12, a blood characteristics calculation section 13, a blood vessel characteristics calculation section 14, a blood flow characteristics calculation section 15, a blood flow analysis execution section 16 and an input interface generation section 17. The data storage section 7 is provided with the blood vessel shape information 21, an appropriate shear stress template 22, a blood characteristics template 23, a blood vessel characteristics template 24, a blood flow characteristics template 25 and a beating rate template 26.

In practice, the above structural requirements (the vascular diameter calculation section 11, the appropriate shear stress calculation section 12, the blood characteristics calculation section 13, the blood vessel characteristics calculation section 14, the blood flow characteristics calculation section 15, the blood flow analysis execution section 16 and the input interface generation section 17) are configured with computer software stored in a storage area of a hard disk, called by the CPU 2, and deployed and executed on the memory 3 to thereby serve as respective components of the present invention.

Now, functions of the respective components 11-16 will be outlined, wherein the vascular diameter calculation section 11 first obtains medical images 21 from an imager (not shown) (Step S1-1), and calculates a vascular diameter of an inlet/outlet blood vessel of the object blood vessel region (Step S1-2). The appropriate shear stress calculation section 12 uses the appropriate shear stress template 22 (Step S2-1) to calculate an appropriate shear stress imparted on the object blood vessel region based on a user-specified condition (Step S2-2). Next, the blood characteristics calculation section 13 uses the blood characteristics template (Step S3-1) to calculate blood characteristics of the object blood vessel region based on the user-specified condition (Step S3-2). The vascular diameter, the appropriate shear stress and the blood characteristics obtained in Steps S1-S3, respectively, are passed to the blood vessel characteristics calculation section 14. This blood vessel characteristics calculation section 14 applies the received information to the blood vessel characteristics template (Step S4-1) to thereby calculate an average flow rate at the inlet/outlet blood vessel of the object blood vessel region (Step S4-2). Based on the calculated average flow rate at the inlet/outlet blood vessel of the object blood vessel region, the blood flow characteristics calculation section 15 calculates the blood characteristics of the object blood vessel region, namely, temporal flow rate fluctuation of the inlet/outlet blood vessel. Specifically, the blood flow characteristics calculation section 15 uses a blood flow characteristics template and/or a beating rate template, which are prepared based on the user-specified condition (namely, a medical condition, an age of a patient, etc.) (Steps S5-1 and S5-2), and applies the average flow rate at the inlet/outlet blood vessel of the object blood vessel region to the blood flow characteristics template and/or the beating rate template to thereby calculate the temporal flow rate fluctuation at the inlet/outlet blood vessel (Step S5-3). Subsequently, the blood flow analysis execution section 16 uses, as an input, the temporal flow rate fluctuation at the inlet/outlet blood vessel calculated in Step S5 to execute a blood flow analysis for the object blood vessel region.

Note that, although the embodiment described above is configured so that a user specifies the condition in each Step, the embodiment may be configured so that the input interface generation section 16 is used to generate an input interface allowing the user to specify all required conditions for respective templates at once.

Next, the operation performed by each component will be described step by step in detail with reference to FIGS. 3-10.

Vascular Diameter Calculation Section (Step S1)

Figure 3:
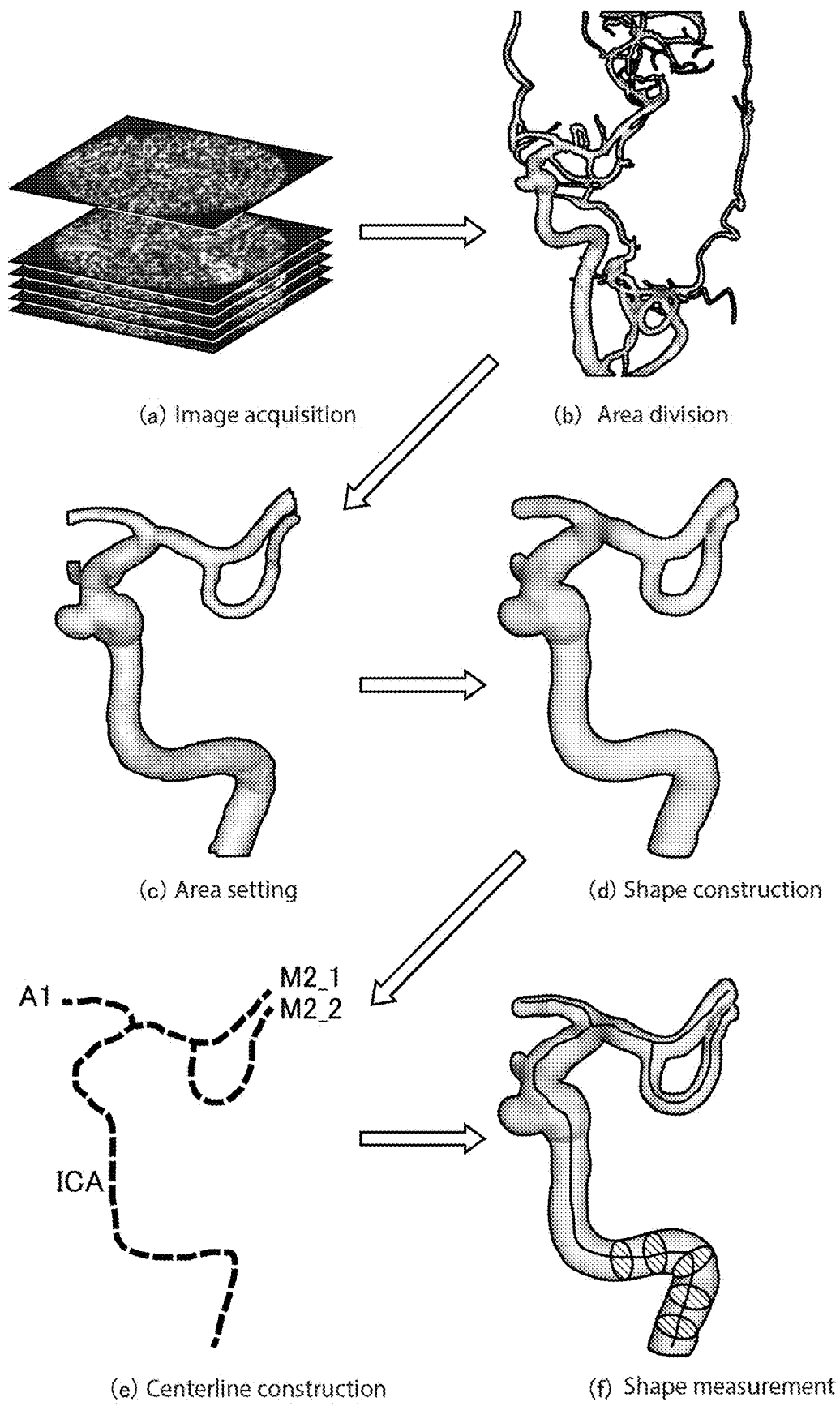
FIGS. 3 (a)-(f) are diagrams describing steps of calculating a vascular diameter from medical images.
Figure 4:
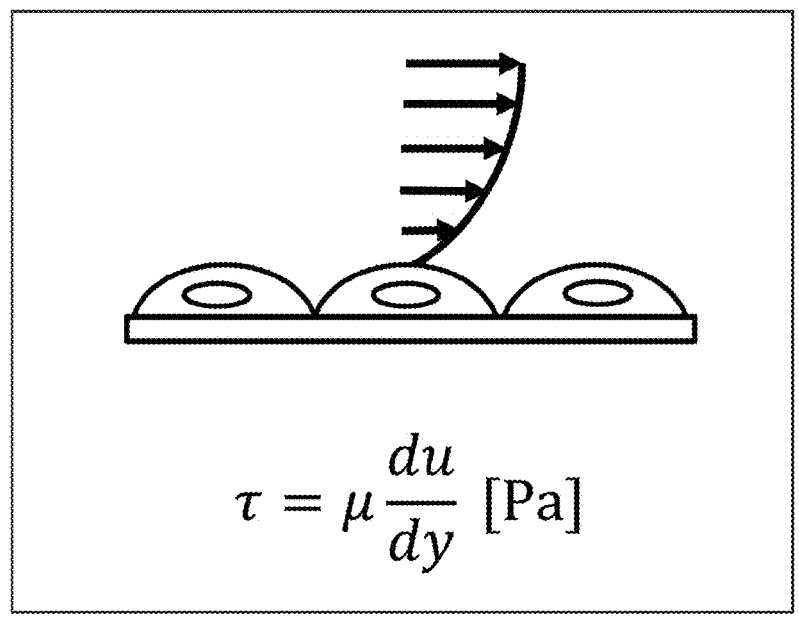
FIG. 4(a) is a schematic diagram describing a wall surface shear stress.
FIG. 4(b) is an example of an appropriate wall surface shear stress template in one embodiment of the present invention.
Figure 5:
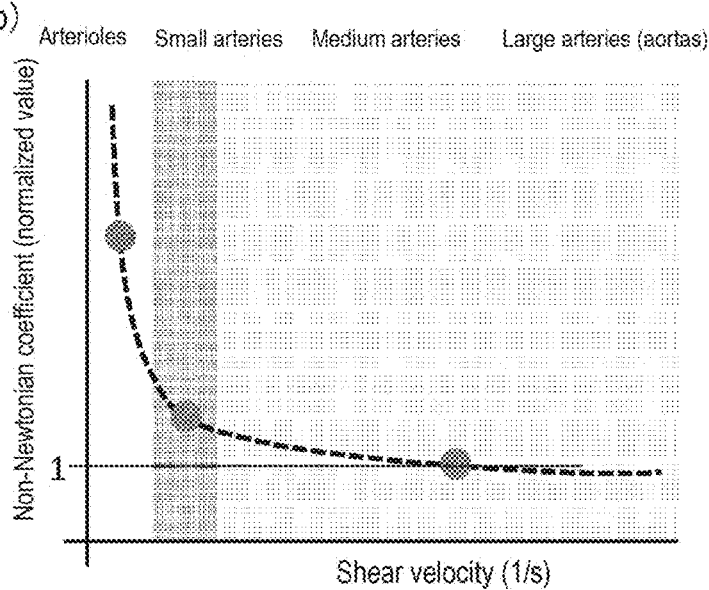
FIG. 5(a) is an example of a blood characteristics template in one embodiment of the present invention.
FIG. 5(b) is a diagram showing a relationship between object blood vessels and the non-Newtonian coefficient.
Figure 6:
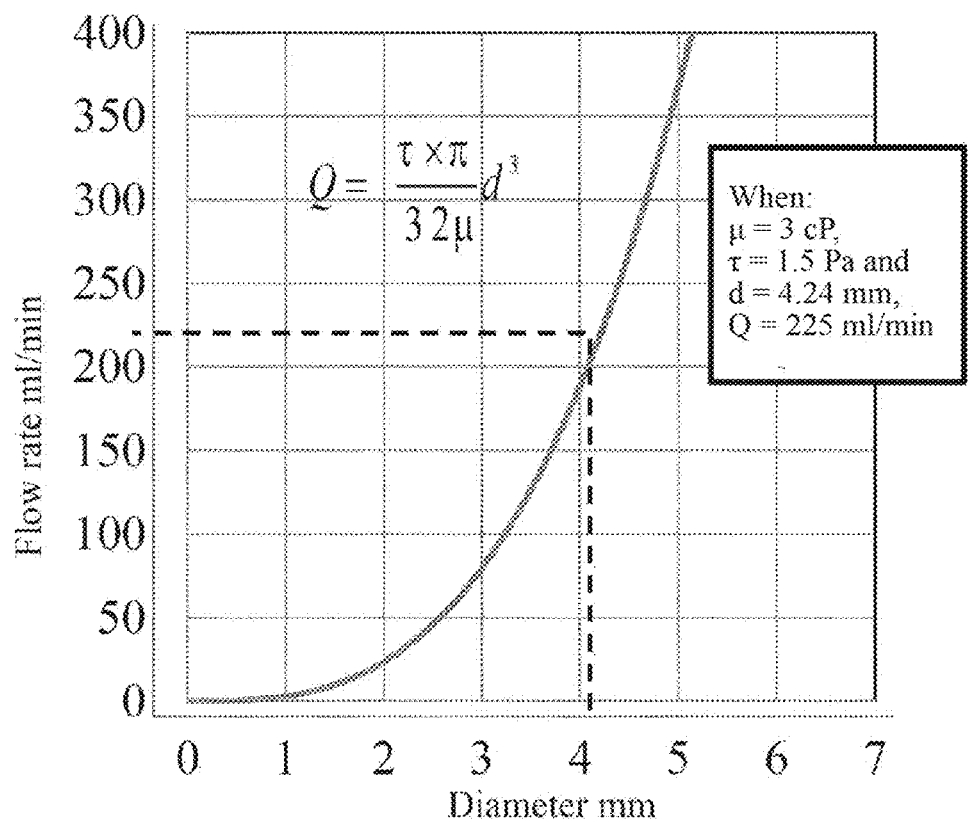
FIG. 6 is a diagram showing an example of average flow rate calculation in one embodiment of the present invention.

FIGS. 3 (a)-(f) are schematic diagrams showing processing at the vascular diameter calculation section 11.

This vascular diameter calculation section 11 first obtains medical images which include the object blood vessel from the imager (FIG. 3(a)). Here, the imager refers to one providing MRA (magnetic resonance angiography images), CTA (computed tomography angiography images), DSA (digital subtraction angiography images), IVUS (intravascular ultrasound images), OCT (optical coherence tomography images) and the like, but any imager capable of extracting a 3D shape of a blood vessel may be used.

Next, the blood vessels are extracted from the medical images using the 3D volume rendering (FIG. 3(b)). In this case, blood vessel-specific signals are extracted, but other methods may be used such as the threshold method using signal values themselves or the gradient method using spatial change of signals.

Next, the object blood vessel used for blood flow analysis is extracted (FIG. 3(c)). This extraction is performed according to the user specification (based on mice, etc.) or performed automatically (automatic determination in the object blood vessel area). In this example, a brain artery is specified. Also, with this specification, the object blood vessel inlet/outlet is determined.

Next, blood vessel curves are formed using the marching cubes method or the like (FIG. 3(d)). Thus, an image voxel space is converted to a polygonal space. In other words, blood vessel walls are composed of minute triangle elements at this point.

Next, a centerline is constructed for each blood vessel (FIG. 3(e)). There are many method reported for extracting centerlines, but there is no limitation as to which method should be used here. Next, a name is give to each inlet/outlet blood vessel (FIG. 3(e)).

After naming the blood vessels, their shapes are measured (FIG. 3(f)). During this measurement here, an orthogonal cross section is generated at each point of each centerline, and the change in the cross-sectional area is calculated for each blood vessel. Based on a diameter (equivalent diameter) obtained by assuming a circle equivalent to each cross-sectional area value, an inlet/outlet vascular diameter is determined. Here, it may be an end face diameter, or a median or an average value may be used.

Appropriate Shear Stress Calculation Section (Step S2)

The appropriate shear stress calculation section 12 determines the appropriate shear stress by having the user select a predetermined condition from the appropriate shear stress template 22 prepared by a computer.

Here, to describe the shear stress based on FIG. 4(a), vascular endothelial cells in the illustrated vascular luminal surface control the contraction or expansion of the vascular diameter, or negative or positive blood vessel remodeling, by sensing the blood flow shear stress. That is, the endothelial cells regulate the vascular diameter to achieve the appropriate shear stress according to the state of the endothelial cells. In this case, the shear stress may be calculated by the product of the blood viscosity $\mu$ and a velocity gradient du/dy as in the formula of FIG. 4(a).

In this embodiment, as shown in FIG. 4(b), the appropriate shear stress (Pa) is provided by the appropriate shear stress template 22 associated with "aging advancement and medical condition." Numeric values in the template are statistical average values calculated from experiments. The appropriate shear stress template 22 uses standard values as baselines and each standard value is associated with the aging advancement. Further, the appropriate shear stress template 22 selects presence/absence of a medical condition. Here, the appropriate shear stress is obtained by modifying the baseline values according to the degrees of arteriosclerosis and hypertension. For each patient, if a standard value C and a low degree of hypertension (indicated with "+" in the figure) are selected for example, the standard value is calculated as 5.0×1.3=6.5 to yield the appropriate shear stress.

Therefore, in order to select the appropriate shear stress template 22, this appropriate shear stress calculation section 12 preferably provides the user (a patient, a physician or an operator of the present system) with an input interface for "aging advancement" and "medical condition" with, for example, options to choose from. Alternatively, the system may automatically input the values. Information (selections) of the "aging advancement" and the "medical condition" entered here will be also used later by the blood characteristics calculation section 13 and the blood flow characteristics calculation section 15.

Blood Characteristics Calculation Section (Step S3)

The blood characteristics calculation section 13 calculates the blood characteristics by having the user select a predetermined condition from the blood characteristics template 23, as shown in FIG. 5(a), prepared by the computer. The blood characteristics refers to blood density and viscosity. Here, the blood characteristics template 23, which associates the blood characteristics with the aging advancement and medical condition, is provided. Numeric values in the template are statistical average values calculated from experiments.

The blood characteristics template 23 uses standard values as baselines and each standard value is associated with the aging advancement.

Therefore, for the selection using the blood characteristics template 23, this embodiment further provides an interface for allowing the user or the like to select presence/absence of hematologic disease, disease types (hyperlipemia and diabetes in this embodiment), presence/absence and a degree of drug administration (antiplatelet agent and anticoagulant in this embodiment) and object blood vessels (here, the object blood vessels are large, medium and small arteries; and arterioles).

Here, to describe the relationship between the object blood vessel and the viscosity, the standard viscosity (i.e., the baseline) is a blood viscosity at a high shear area, where the blood viscosity doesn't depend on a shear velocity. Whereas, it is know that the blood viscosity increases as the shear velocity decreases. In other words, smaller blood vessels have lower blood vessel flow rates, and the smaller the blood vessel is, the higher the viscosity becomes. Consequently, selecting the object blood vessel means making a viscosity correction. Relative values are provided with the standard viscosity being 1. These relative values are called non-Newtonian coefficients. Referring to FIG. 5(b), when a small artery is selected, for example, an average coefficient is selected from the shear velocity area of small arteries.

Blood Characteristics Calculation Section (Step S4)

The blood vessel characteristics calculation section 14 provides the blood vessel characteristics template 24 (in this example, the model formula below (FIG. 6)), prepared by the computer, with the values calculated in the above Steps S1-S3 (vascular diameter, shear stress and viscosity) to thereby calculate the average flow rate of the inlet/outlet blood vessel of the object blood vessel.

Here, the above model formula associates factors such as the appropriate shear stress, the blood characteristics (i.e., the density and the viscosity) and the vascular diameter with the average flow rate. Each factor's value is output ahead of time as discussed above, and used by being substituted into the model formula.

In other words, inlet and outlet flow rates the object blood vessel may be calculated from inlet and outlet diameters of the object blood vessel, respectively. For example, assuming that the viscosity $\mu=3$ cP, the appropriate shear stress $\tau=1.5$ Pa and d=4.24 mm, the average flow rate Q=225 ml/min is calculated from the above model formula.

Demonstration Test A of Blood Characteristics Calculation Section

Figure 7:
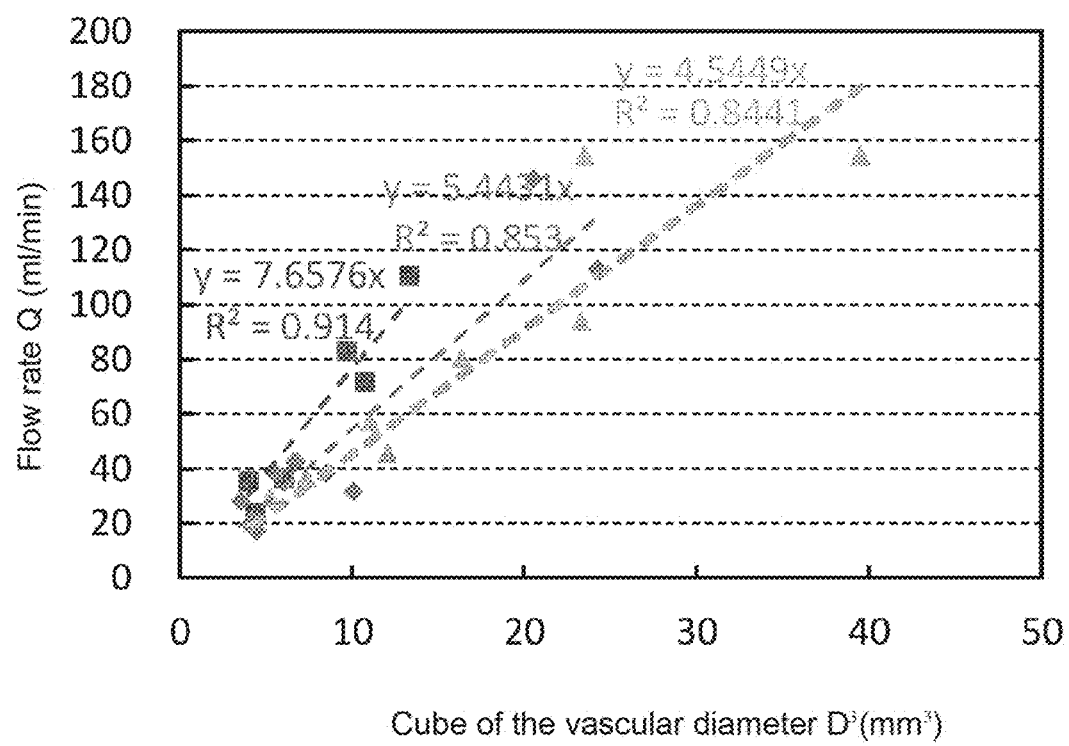
FIG. 7 is a diagram showing data demonstrating the relationship between the vascular diameter and the flow rate.

The graph of FIG. 7 demonstrates that the cube of the vascular diameter is proportional to the flow rate. Here, cerebral blood vessels of healthy volunteers were measured. The number of subjects is three. For each subject, 5-7 locations on the blood vessel were measured. For example, those locations are on middle cerebral arteries or anterior cerebral arteries. The phase-contrast MRI method was used for the flow rate measurement. Similarly, the vascular diameter was obtained by the MRI method using the equivalent diameter. For each subject, it is shown that the flow rate and the cube of vascular diameter are proportional to each other although the slope may vary.

Demonstration Test B of Blood Characteristics Calculation Section

Figure 8:
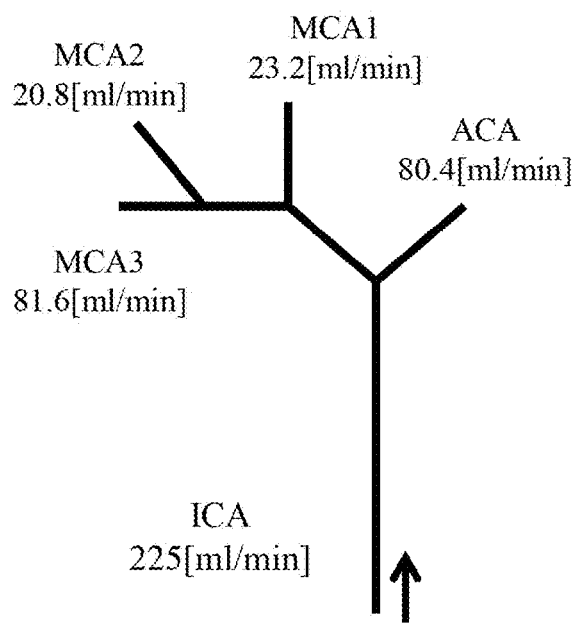
FIGS. 8(a) and (b) are diagrams showing comparisons between calculated values from a blood vessel characteristics calculation section and demonstration data.
Figure 9:
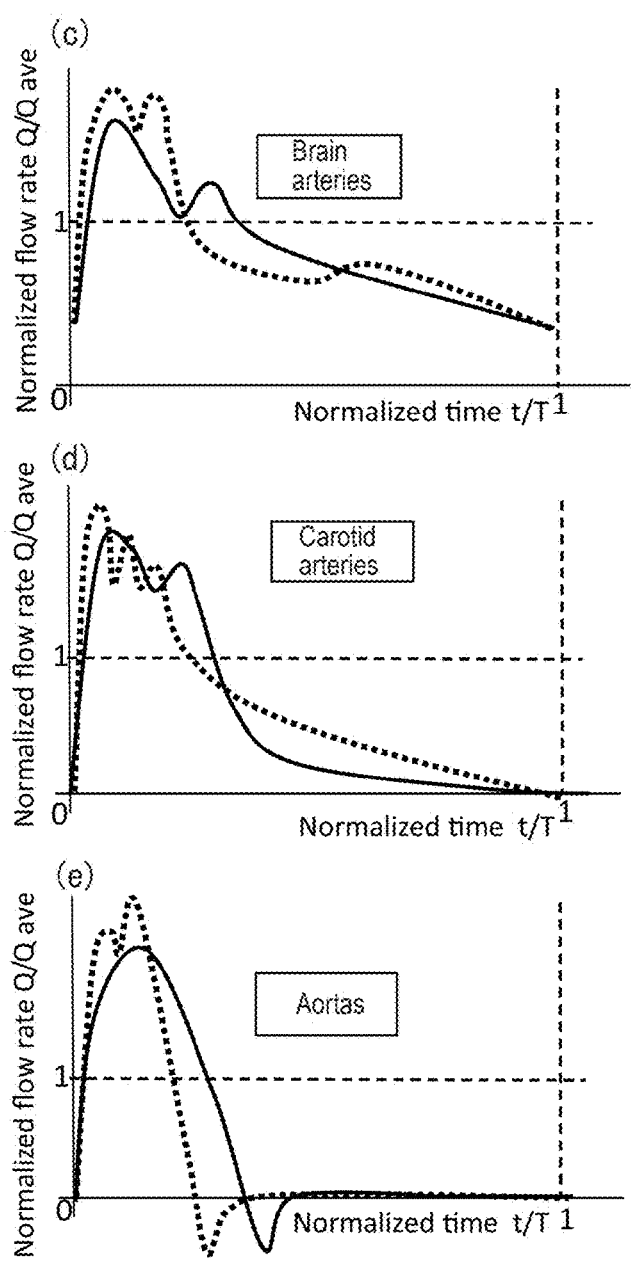
FIG. 9(a) is an example of a blood flow characteristics template.
FIG. 9(b) is an example of a heart rate template.
FIGS. 9(c)-(e) are diagrams showing examples of a temporal flow rate fluctuation pattern.
Figure 10:
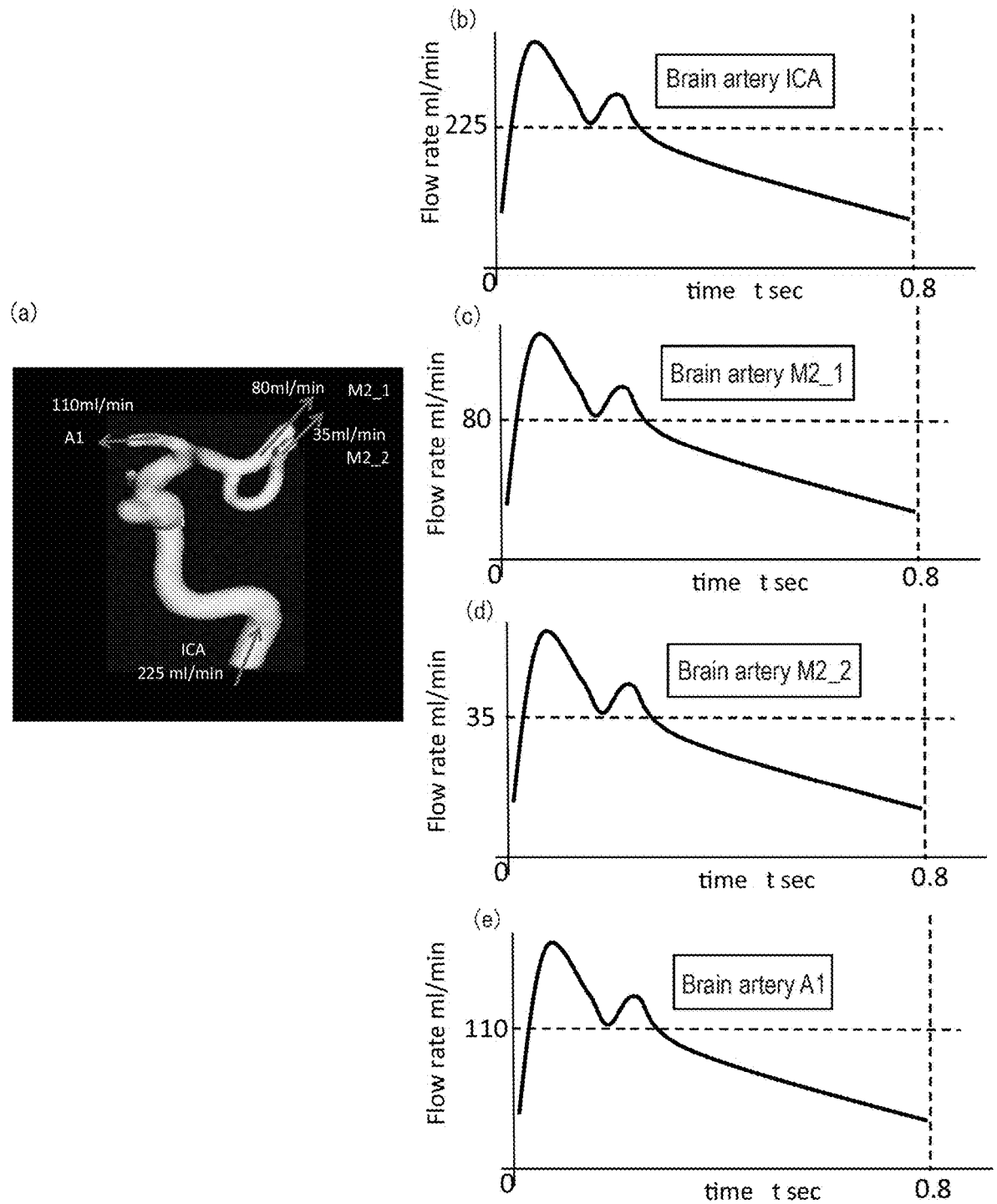
FIG. 10(a) is an example of an output superimposing calculation results of a blood flow characteristics calculation section onto the object blood vessel region.
FIGS. 10(b)-(e) are diagrams showing the calculation results of the blood flow characteristics calculation section.

Data in FIGS. 8 (a) and (b) demonstrate that estimated average flow rates obtained with the above Steps S1-S4 are effective. Here, average flow rates calculated for a subject are compared with values in the reference literature. Each of the reference values is an average flow rate of a plurality of volunteers for each blood vessel. Referring to the average values first, the reference values and calculated values match well with each other for all of vessels ICA, MCA and ACA, respectively. Here, the value for MCA is calculated as a sum of three branches (MCA1, MCA2 and MCA3) shown in FIG. 8(a). Further, referring to a flow rate distribution ratio, the calculated values show the validity of the assumption that the cube of the vascular diameter and the flow rate are proportional to each other as discussed above. In other words, the flow rate distribution ratio for ACA clearly shows a successful match between the reference and calculated values.

Blood Flow Characteristics Calculation Section (Step S5)

The blood flow characteristics calculation section 15 calculates blood flow characteristics of the object blood vessel region, namely, the temporal flow rate fluctuation of the inlet/outlet blood vessel based on the estimated average flow rates derived from Step S4. Specifically, the blood flow characteristics calculation section 15 uses the blood flow characteristics template 25 and/or the beating rate template 26, which are prepared based on the user-specified condition (namely, the medical condition, the age of a patient, etc.) (Steps S5-1 and S5-2), and applies the average flow rate at the inlet/outlet blood vessel of the object blood vessel region to the blood flow characteristics template and/or the beating rate template to thereby calculate the temporal flow rate fluctuation at the inlet/outlet blood vessel (Step S5-3).

In this example, a blood flow characteristics template (temporal flow rate fluctuation pattern) is used, wherein the temporal flow rate fluctuation at the blood vessel inlet/outlet is associated with the blood vessel region, aging advancement and medical condition. As shown in FIGS. 9(c)-(e), the blood flow characteristics template 26 represents normalized data with non-dimensional time as its horizontal axis and non-dimensional flow rate as its vertical axis. Numeric values of the horizontal and vertical axes are obtained by non-dimensionalizing experiment data to indicate a temporal blood flow rate fluctuation pattern with statistical average values. Here, the non-dimensionalization of the horizontal axis is based on one cardiac pulsation period in order to consider various heart rates for different subjects. Here, the non-dimensionalization of the vertical axis is based on the average flow rate in order to consider various average flow rates for different subjects.

In Step S5-1, the present system first selects a baseline based on a blood vessel region type (brain artery, carotid artery, aortic artery, etc.) entered by the user. As indicated with solid lines in FIGS. 9(c)-(e), the baselines provide different temporal flow rate fluctuations as normalized values for each site such as a brain artery or a carotid artery.

Next, this system corrects the baselines, as indicated with broken lines in FIGS. 9(c)-(e), using an aging advancement and medical condition information template for associating the user-entered aging advancement and medical condition (arteriosclerosis and hypertension), and a heart rate template for associating the heart rate.

In this example, as shown in FIG. 9(a), the user provides five types of information which may be selected and entered as the aging advancement and medical condition information, namely: arteriosclerosis (two types) and hypertension (two types), and as the heart rate information, standard, low heart rate (two types) and high heart rate (two types).

Thus, by selecting the aging advancement and medical condition, and the heart rate, the blood flow rate fluctuation template (the broken lines in FIGS. 9(c)-(e)), applied to the average flow rate obtained in Step S4, may be obtained (Step S5-3).

Output of Blood Flow Characteristics Calculation Section (In Case of Brain Artery)

Finally, by applying the estimated average flow rate at the inlet/outlet of the object blood vessel obtained in the above Step S4 as the average flow rate of the blood flow rate fluctuation template (the broken lines in FIGS. 9(c)-(e)), the temporal flow rate fluctuation at each inlet/outlet of the object blood vessel region may be obtained, as shown in FIGS. 10(b)-(e). Note that the examples of FIGS. 10(b)-(e) are of brain arteries based on values of healthy subjects.

Needless to say, the present invention may be modified in various manners and is not limited to the above one embodiment, and various changes and modifications may be made without departing from the scope and spirit of the invention.

What is claimed is:

1. A method for executing a computational fluid analysis on a blood flow in a blood vessel region to be analyzed, and displaying analysis results, comprising the steps of:
    obtaining, by a computer, a vascular diameter (d) of an inlet and/or outlet of a blood vessel region to be analyzed from medical images which include said blood vessel region;
    obtaining, by the computer, an estimated flow rate (Q) at the inlet and/or outlet based on the vascular diameter (d); and
    applying, by the computer, the estimated flow rate (Q) to a blood flow characteristics pattern of said blood vessel region and outputting blood flow characteristics at the inlet and/or outlet of said blood vessel region.

2. The method of claim 1, further comprising the steps of:
    causing a user, by the computer, to selectively enter an aging advancement, a medical condition, a heart rate and/or an object blood vessel type of a patient as a subject of the blood flow analysis,
    wherein the blood flow characteristics pattern is an individualized pattern prepared according to the user-entered aging advancement, medical condition, heart rate and/or object blood vessel type of the patient, and
    wherein the outputting the blood flow characteristics step is performed by outputting the blood flow characteristics using the blood flow characteristics pattern according to the user-entered aging advancement, medical condition, heart rate and/or object blood vessel type of the patient.

3. The method of claim 1, wherein
the blood flow characteristics pattern is provided to define a relationship between a non-dimensional flow rate on one axis and a non-dimensional time on the other axis.

4. The method of claim 1, wherein
the obtaining the estimated flow rate (Q) step obtains the estimated flow rate (Q) based on a cube of the vascular diameter ($d^3$).

5. The method of claim 4, wherein
the obtaining the estimated flow rate (Q) step obtains the estimated flow rate (Q) based on a following formula:

$$Q=(\tau\times\pi/32\mu)d^3$$

wherein, $\tau$ is an appropriate wall surface shear stress and $\mu$ is a blood viscosity.

6. The method of claim 5, further comprising the steps of:
    causing a user, by the computer, to enter an aging advancement, a medical condition, a heart rate and/or an object blood vessel type of a patient as a subject of the blood flow analysis; and
    determining, by the computer, the appropriate wall surface shear stress ($\tau$) and/or the blood viscosity ($\mu$) based on the user-entered aging advancement, medical condition, heart rate and/or object blood vessel type of the patient.

7. The method of claim 6, wherein
the determining the appropriate wall surface shear stress ($\tau$) and/or the blood viscosity ($\mu$) step uses an appropriate shear stress template and/or a blood characteristics template, which is normalized for each of the aging advancement, medical condition, heart rate and/or object blood vessel type of the patient.

8. The method of claim 1, wherein
the vascular diameter (d) is calculated by the computer as an equivalent diameter of an assumed circle having an identical area with a measured area of a plane orthogonal to a blood vessel centerline, wherein an average value or a median is used for the equivalent diameter.

9. The method of claim 1, wherein
the blood flow characteristics pattern is a temporal flow rate fluctuation pattern, and the blood flow characteristics is a temporal flow rate fluctuation.

10. A blood flow analysis apparatus for executing a computational fluid analysis on a blood flow in a blood vessel region to be analyzed, and displaying the analysis results, comprising:
    a vascular diameter calculation section for obtaining, by a computer, a vascular diameter (d) of an inlet and/or outlet of a blood vessel region to be analyzed from medical images which include said blood vessel region;

a blood vessel characteristics calculation section for obtaining, by the computer, an estimated flow rate (Q) at the inlet and/or outlet based on the vascular diameter (d); and a blood flow characteristics calculation section for applying, by the computer, the estimated flow rate (Q) to a blood flow characteristics pattern of said blood vessel region and outputting blood flow characteristics at the inlet and/or outlet of said blood vessel region.

11. The blood flow analysis apparatus of claim 10, further comprising:

an input section for causing a user, by the computer, to selectively enter an aging advancement, a medical condition, a heart rate and/or an object blood vessel type of a patient as a subject of the blood flow analysis, wherein the blood flow characteristics pattern is an individualized pattern prepared according to the user-entered aging advancement, medical condition, heart rate and/or object blood vessel type of the patient, and wherein the blood flow characteristics calculation section for outputting the blood flow characteristics outputs the blood flow characteristics using the blood flow characteristics pattern according to the user-entered aging advancement, medical condition, heart rate and/or object blood vessel type of the patient.

12. The blood flow analysis apparatus of claim 10, wherein the blood flow characteristics pattern is provided to define a relationship between a non-dimensional flow rate on one axis and a non-dimensional time on the other axis.

13. The blood flow analysis apparatus of claim 10, wherein the blood vessel characteristics calculation section for obtaining the estimated flow rate (Q) obtains the estimated flow rate (Q) based on a cube of the vascular diameter ($d^3$).

14. The blood flow analysis apparatus of claim 13, wherein the blood vessel characteristics calculation section for obtaining the estimated flow rate (Q) obtains the estimated flow rate (Q) based on the following formula:

$$Q = (\tau \times \pi / 32\mu) d^3$$

wherein, $\tau$ is an appropriate wall surface shear stress and $\mu$ is a blood viscosity.

15. The blood flow analysis apparatus of claim 14, further comprising:

an input section for causing a user, by the computer, to selectively enter an aging advancement, a medical condition, a heart rate and/or an object blood vessel type of a patient as a subject of the blood flow analysis; and an appropriate wall surface shear stress calculation section for determining the appropriate wall surface shear stress ($\tau$) and/or a blood characteristics calculation section for determining the blood viscosity ($\mu$), wherein both determinations are performed by the computer based on the user-entered aging advancement, medical condition, heart rate and/or object blood vessel type of the patient.

16. The blood flow analysis apparatus of claim 15, wherein the appropriate wall surface shear stress calculation section for determining the appropriate wall surface shear stress ($\tau$) and/or the blood characteristics calculation section for determining the blood viscosity ($\mu$) use an appropriate shear stress template and/or a blood characteristics template, which is normalized for each of the aging advancement, medical condition, heart rate and/or object blood vessel type of the patient.

17. The blood flow analysis apparatus of claim 10, wherein the vascular diameter (d) is calculated by the computer as an equivalent diameter of an assumed circle having an identical area with a measured area of a plane orthogonal to a blood vessel centerline, wherein an average value or a median is used for the equivalent diameter.

18. The blood flow analysis apparatus of claim 10, wherein the blood flow characteristics pattern is a temporal flow rate fluctuation pattern, and the blood flow characteristics is a temporal flow rate fluctuation.

* * * * *